United States Patent
Lawrence et al.

(10) Patent No.: US 9,375,467 B2
(45) Date of Patent: Jun. 28, 2016

(54) LIVE ATTENUATED CATFISH VACCINE AND METHOD OF MAKING

(71) Applicants: Mark L. Lawrence, Starkville, MS (US); Attila Karsi, Starkville, MS (US)

(72) Inventors: Mark L. Lawrence, Starkville, MS (US); Attila Karsi, Starkville, MS (US)

(73) Assignee: Mississippi State University, Mississippi State, MS (US)

( * ) Notice: Subject to any disclaimer, the term of this patent is extended or adjusted under 35 U.S.C. 154(b) by 0 days.

(21) Appl. No.: 13/940,125

(22) Filed: Jul. 11, 2013

(65) Prior Publication Data

US 2013/0295136 A1 Nov. 7, 2013

Related U.S. Application Data

(62) Division of application No. 12/490,207, filed on Jun. 23, 2009, now Pat. No. 8,507,278.

(60) Provisional application No. 61/074,813, filed on Jun. 23, 2008.

(51) Int. Cl.
| | |
|---|---|
| *C12N 15/10* | (2006.01) |
| *A61K 39/02* | (2006.01) |
| *A61K 39/00* | (2006.01) |

(52) U.S. Cl.
CPC ............ *A61K 39/025* (2013.01); *C12N 15/102* (2013.01); *A61K 2039/522* (2013.01); *A61K 2039/552* (2013.01)

(58) Field of Classification Search
None
See application file for complete search history.

(56) References Cited

PUBLICATIONS

Ellis, R.W. (Chapter 29 of "Vaccines" [Plotkin, S.A. et al. (eds) published by W. B. Saunders company (Philadelphia) in 1988, p. 568-575.*
Karsi et al. (Appl. Environ. Microbiol., 75:2166-2175, 2009).*
Mercado-Lubo (Infect. Immun., 76:1128-1134; 2008).*
Courtright and Henning (Courtright et al., J. Bacteriol., 102:722-728, 1970).*
Yimga et al. (Infect. Immun., 74:1130-1140).*

* cited by examiner

*Primary Examiner* — Brian J Gangle
(74) *Attorney, Agent, or Firm* — Butler Snow LLP

(57) ABSTRACT

A high throughput bioluminescence mutant screening procedure is disclosed. This procedure utilizes robotics, and bacterial luciferase to allow real-time monitoring of mutant viability. The procedure was used to decelop a live attenuated vaccine for a catfish against *E. ictaluri*, which is further claimed herein. Additionally, genes from other bacterial species are disclosed which may also be used to create vaccines.

15 Claims, 3 Drawing Sheets

FIG. 1

*E. ictaluri* Genome (~3945ORFs)
↓ *MAR2XT7* Mutagenesis
Mutant Library (~15,000 Mutants)
↓
1st In Vitro BLMS of 2256 Mutants
↓
2nd In Vitro BLMS of 180 Mutants
↓
1st In Vivo Screening of 100 Mutants
↓
2nd In Vivo Screening of 14 Mutants
↓
Insertion Site Identification
↓
Vaccine Development

*Edwardsiella ictaluri genome*
~3.88 Mb

LIVE ATTENUATED CATFISH VACCINE AND METHOD OF MAKING

FEDERALLY SPONSORED RESEARCH

This invention was made with government support under 2004-35204-14211 awarded by the Cooperative State Research, Education, and Extension Service, USDA. The government has certain rights in the invention.

FIELD OF THE INVENTION

The present invention is generally directed toward a live attenuated vaccine for catfish. More particularly, it is directed toward a method for using bioluminescence to identify genes required for host resistance in bacteria. Genes that may be used to make live attenuated vaccines in bacteria are also disclosed.

BACKGROUND OF THE INVENTION

Functional genomics has enabled high-throughput methods for identifying bacterial genes and proteins that are differentially expressed in response to host defenses. In particular, both microarrays and high throughput proteomics have been used to identify bacterial genes associated with resistance to host defenses. In addition to microarrays and proteomics, other high-throughput methods have been used to identify bacterial genes upregulated in response to phagocytosis, including differential fluorescence induction (DFI), random luciferase transcriptional fusions, and selective capture of transcribed sequences (SCOTS).

However, genes that are differentially regulated in response to a host defense are not necessarily the same as those that are required for survival. For example, not all of the genes that have increased expression following phagocytosis are required for survival in phagocytes. It is also possible that not all of the genes required for survival have enough change in expression to allow detection. Therefore, mutagenesis studies complement gene and protein expression studies and are likely to detect a unique set of genes that are required for survival.

A major hurdle in identifying bacterial mutants susceptible to host defenses is that the screening methods tend to be labor intensive. Fields et al. identified 83 *S. typhimurium* transposon mutants with impaired macrophage survival by screening individual transposon mutants with phagocytes in 96-well plates (Fields, P. I., Swanson, R. V., Haidaris, C. G. & Heffron, F. Mutants of *Salmonella typhimurium* that cannot survive within the macrophage are avirulent. *Proc Natl Acad Sci USA* 83, 5189-5193 (1986)). However, this assay required bacterial quantification from each well by plate counts. Zhao et al. used the same method to identify 37 *Salmonella* mutants susceptible to chicken macrophages (Zhao, Y. et al. Identification of genes affecting *Salmonella enterica* serovar Enteritidis infection of chicken macrophages. *Infect Immun* 70, 5319-5321 (2002)).

Improvements to allow high-throughput mutant screening have been reported, including a method for screening of bacterial mutants using bioluminescence to identify mycobacterial genes required for survival in macrophages and a microarray-based method for screening mutants. However, none of the previously described methods allow monitoring of bacterial mutant viability at multiple time points. In addition, previous bioluminescence based methods required a bacterial lysis step and addition of extraneous luciferin substrate and ATP for determining luciferase activity, which increases handling and cost while reducing the screening efficiency.

*Edwardsiella ictaluri* is the causative agent of enteric septicemia of catfish, an important disease of farm-raised channel catfish. Like some other species in the *Enterobacteriaceae*, *E. ictaluri* has the ability to resist killing by professional phagocytes. In particular, *E. ictaluri* is resistant to channel catfish neutrophils, which is an important aspect of pathogenesis because neutrophils are the predominant cell type in channel catfish intestinal tract immune cells. The intestine is an important site of entry for *E. ictaluri*. *E. ictaluri* is also resistant to killing by the alternative complement pathway in channel catfish.

There exists a need for a high throughput method for screening bacterial mutants to be used in live attenuated vaccines, such as one against *Edwardsiella ictaluri* in catfish.

SUMMARY OF THE INVENTION

A high throughput bioluminescence mutant screening (BLMS) method that is not labor intensive and that allows real-time monitoring of mutant viability is disclosed. Robotics was used to array mutants into 96 well plates, reducing manual labor. In addition, bacterial luciferase was used instead of firefly luciferase, which allays the need for addition of luciferin substrate and allows real-time monitoring of mutant viability. The resulting BLMS procedure allows collection of data from multiple time points for real-time screening of bacterial mutants against multiple host defense mechanisms. We utilized BLMS to identify *E. ictaluri* mutants that are susceptible to killing by channel catfish neutrophils and serum. Fourteen of the mutants were attenuated in channel catfish, and those that were completely attenuated were effective as live attenuated vaccines, demonstrating the utility of BLMS for vaccine development. These vaccines are disclosed as a patentable invention. Additional genes from other bacterial species that also may be used as live attenuated vaccines are also disclosed herein.

BRIEF DESCRIPTION OF THE DRAWINGS

Further advantages of the invention will become apparent by reference to the detailed description of preferred embodiments when considered in conjunction with the drawings, which are not to scale, wherein like reference characters designate like or similar elements to the several drawings as follows:

FIG. 1 depicts an overview of mutant screening procedures.

DETAILED DESCRIPTION OF THE PREFERRED EMBODIMENT

Figure 2:
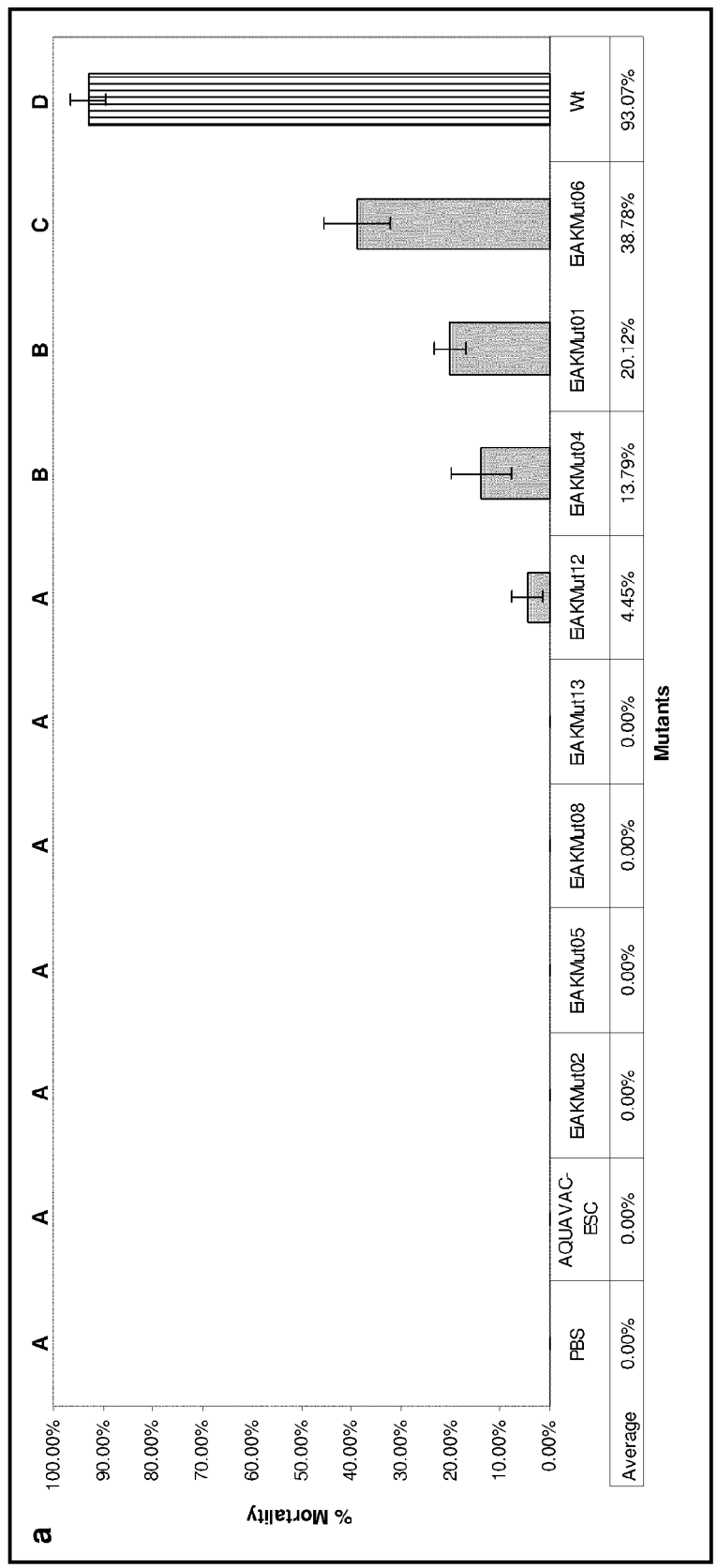
FIG. 2 depicts the results of vaccine efficacy trial and shows the percent mortalities resulting from vaccination. Percent mortalities are the mean of four replicate tanks per treatment. PBS is saline control, Wt is parent strain 93-146, and AQUAVAC-ESC is a commercial live attenuated vaccine. Capital letters above each bar indicate statistical groupings. Groups marked with the same capital letter do not show statistically significant differences ($P<0.05$).

The BLMS method claimed herein was successfully used in the development of a vaccine for channel catfish against *E. ictaluri*. Although the foregoing embodiment describes the claimed methods as applied in vaccine development against *E. ictaluri*, the BLMS method is widely applicable to the screening of any bacterial species.

Technological developments in functional genomics allow detection of molecular phenotypes that evade detection at the physiological or morphological levels. We disclose a new high-throughput functional genomics tool that we call bioluminescence mutant screening (BLMS) that translates molecular genotypes (gene mutations) to physiological phenotypes (light production) in bacteria and allows application of forward genetics.

BLMS involves random transposon mutation of a bacterial strain expressing bacterial luciferase operon (luxCDABE) in a stable plasmid. Following this approach, we produced a random *E. ictaluri* mutant library that conditionally expresses luxCDABE genes from a stable plasmid, pAKgfplux2, which allows the tracking of mutants in a pool under different experimental conditions.

In an alternative embodiment, luxCDABE genes could also be incorporated into bacterial chromosomes for a similar BLMS purpose. Chromosomal insertion of luxCDABE operon may require more sensitive instrumentation to alleviate the reduced amount of bioluminescence produced from a single copy lux operon. Our BLMS procedure requires use of IPTG because our mutant library expresses lux operon conditionally from a lacZ promoter on pAKgfplux2, which also carries a lad$^q$ suppressor gene. To eliminate use of IPTG in bacterial strains without the presence of lac$^q$ gene in their genome use of a mutant library constitutively expressing lux operon from a stable plasmid, such as pAKlux2 and pAKgfplux1, would be preferred.

Through screening 2,256 mutants from *E. ictaluri* mutant library, we were able to identify 14 attenuated mutants at the end of in vitro BLMS and in vivo fish screening. Eight mutants were common to neutrophil and serum screening while only four and only two mutants were identified as neutrophil and serum mutants, respectively. The fourteen identified *E. ictaluri* mutants were first characterized in terms of their virulence and vaccine potential and later mutated genes in each mutant were determined by transposon insertion sites identification. Finally, selected mutants were compared to a commercial vaccine (AQUAVAC-ESC) to determine their commercial value. Findings from our research suggest that BLMS is a very powerful screening method for development of live attenuated vaccines. Fourteen mutants identified by utilizing BLMS showed reduced virulence as compared to wild type *E. ictaluri* and provided increased protection from ESC compared to non-vaccinated controls. Among the 14 mutants, we observed redundant mutations in two genes. Three different mutants harbored transposon insertion at different locations in gcvP, which encodes glycine cleavage system protein P. Two different mutants harbored transposon insertion at the same location in rseB, which encodes a negative regulator of sigma E activity. This provides confirmation that BLMS procedure is a sensitive method detecting true targets.

BLMS can detect novel virulence relevant genes located on native plasmids or show importance of native plasmids in bacterial virulence if random mutation occurs in the origin of replication of native plasmids. While applying BLMS to *E. ictaluri*, we observed that at least one of the two native plasmids of *E. ictaluri* (pEI1) may be important in *E. ictaluri* virulence because two different locations were targeted on this plasmid in two different mutants (EiAKMut04 and EiAKMut10).

Production of *Edwardsiella ictaluri* Mutant Library

A library of random transposon insertion mutations in conditionally bioluminescent *E. ictaluri* strain 93-146 carrying pAKgfplux2 was generated. The library containing approximately 15,000 mutants was created by using a derivative of the mariner transposon Himar1 carried on pMAR2xT7 plasmid. The library consisted of mutants arrayed in 39 384-well plates. A duplicate of the whole library was also prepared. The produced mutant library is compatible with genetic footprinting of the mutants with transposon-site hybridization (TraSH) analysis.

Identification of Serum and Neutrophil Susceptible *Edwardsiella ictaluri* Mutants We used the high throughput bioluminescence mutant screening (BLMS) procedure to identify virulence relevant genes of gram negative bacteria in vitro. We screened 2,256 mutants against both serum and neutrophils using BLMS and identified 180 mutants exhibiting light reduction during incubation with these host factors. A second round screening of these 180 mutants in quadruplicate samples allowed us to identify 35 serum, 39 neutrophil, and 26 both serum and neutrophil susceptible mutants for in vivo studies. General outline of the integrated procedures including in vitro BLMS and in vivo fish screening applied can be seen in FIG. 1. Injection of catfish with 100 BLMS selected mutants resulted in identification of 14 attenuated mutants including 8 mutants susceptible to both serum and neutrophils, 4 susceptible to neutrophils, and 2 susceptible to serum, which were further characterized in vivo.

Characterization of Virulence and Vaccine Potentials of *Edwardsiella ictaluri* Mutants In vitro BLMS allowed us reduce the number of target mutants to an amenable size for in vivo characterization. Fish were infected with 14 mutants and their attenuation and vaccine potentials were determined (Table 1). Virulence of EiAKMut07 and EiAKMut09 appeared to be higher than other mutants while *E. ictaluri* wild type was the most virulent in immersion immunization. EiAKMut02, EiAKMut07, EiAKMut10, and EiAKMut12 provided more protection than other mutants. Similarly, EiAKMut07 and EiAKMut09 were also the most virulent strains in the injection immunization though they were attenuated as compared to wild type strain. Virulence of second category of mutants in injection immunization ranged from 1.25% to 11.67%, while the third category of mutants including EiAKMut02, EiAKMut03, EiAKMut04, and EiAKMut06 seemed to be not virulent. After immersion infection, efficacy of EiAKMut02, EiAKMut08, and EiAKMut12 were statistically superior to others.

TABLE 1

Summary of in vivo mutant characterization results

| Groups | Immunization$^{Im}$ % M | SE | Wt challenge$^{Im}$ % M | SE | Immunization$^{In}$ % M | SE | Wt challenge$^{In}$ % M | SE |
|---|---|---|---|---|---|---|---|---|
| EiAKMut01 | — | — | 1.32 | 1.32 | 6.67 | 3.33 | 5.46 | 0.10 |
| EiAKMut02 | — | — | — | — | — | — | — | — |
| EiAKMut03 | — | — | 6.35 | 5.01 | — | — | 1.67 | 1.67 |
| EiAKMut04 | — | — | 2.17 | 2.17 | — | — | 1.67 | 1.67 |
| EiAKMut05 | — | — | 1.09 | 1.09 | 1.67 | 1.67 | 3.33 | 3.33 |
| EiAKMut06 | — | — | 2.39 | 1.38 | — | — | 2.63 | 1.52 |
| EiAKMut07 | 1.19 | 1.19 | — | — | 58.33 | 8.82 | 3.03 | 3.03 |
| EiAKMut08 | — | — | 1.32 | 1.32 | 1.67 | 1.67 | — | — |
| EiAKMut09 | 1.25 | 1.25 | 2.44 | 1.41 | 48.33 | 9.47 | 4.44 | 4.44 |
| EiAKMut10 | — | — | — | — | 11.25 | 1.26 | 4.10 | 2.55 |
| EiAKMut11 | — | — | 22.02 | 8.63 | 1.25 | 1.19 | 2.72 | 1.58 |
| EiAKMut12 | — | — | — | — | 10.00 | 2.04 | — | — |
| EiAKMut13 | — | — | 1.00 | 1.00 | 11.67 | 7.25 | 5.85 | 0.48 |
| EiAKMut14 | — | — | 18.78 | 3.80 | 5.00 | 0.22 | 1.75 | 1.75 |
| EiWt | 17.55 | 8.01 | 1.39 | 1.39 | 83.75 | 3.75 | — | — |
| PBS | — | — | 88.73 | 1.69 | — | — | 12.50 | 2.50 |

Im, immersion; In, injection; Wt, wild type *E. ictaluri* 93-146; M, mortality; SE, standard error; —, no mortality observed.

Identification of MAR2xT7 Insertions in *Edwardsiella ictaluri* Genome

MAR2XT7 insertion locations were determined using single primer PCR amplification of transposon ends and nested primer sequencing. We determined the insertion locations of MAR2XT7 and identified disrupted genes from all fourteen mutants (Table 2). Gene identification using database searches indicated that glycine cleavage system protein P (gcvP) was disrupted in three of the mutants (EiAKMut02, EiAKMut03, and EiAKMut08) but at different locations. Similarly, negative regulator of sigma E activity (rseB) gene was mutated at the same location in EiAKMut01 and EiAK-Mut07. Interestingly, two genes located on one of the native plasmids of *E. ictaluri* (pEI1) were also mutated. One of these genes was a putative RNA one modulator protein while the other was a hypothetical protein.

Attenuation and Efficacy of *Edwardsiella ictaluri* Mutants and AQUAVAC-ESC

Figure 3:
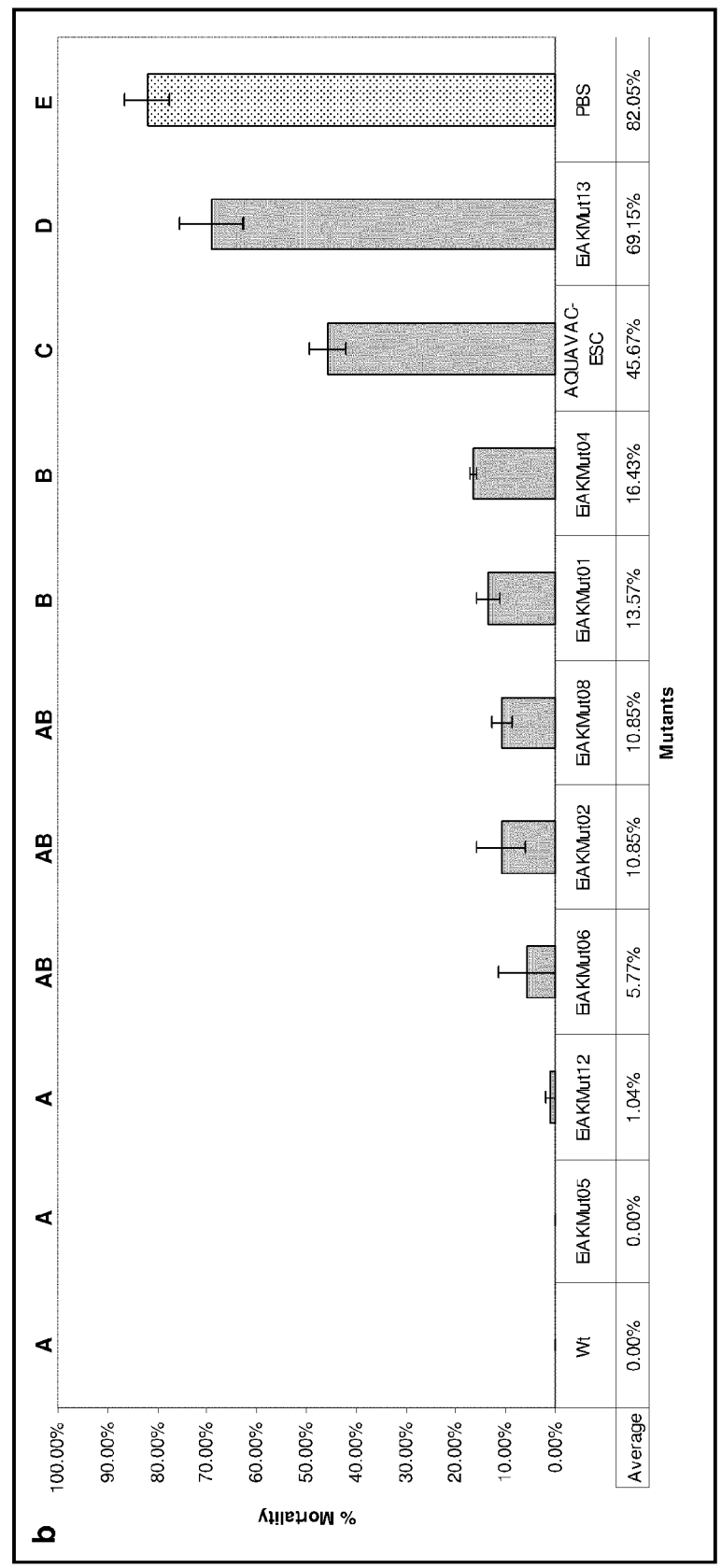
FIG. 3 depicts the results of percent mortalities resulting from challenge with parent strain 93-146 twenty one days post-vaccination. As in the above figure, percent mortalities are the mean of four replicate tanks per treatment. PBS is saline control, Wt is parent strain 93-146, and AQUAVAC-ESC is a commercial live attenuated vaccine. Capital letters above each bar indicate statistical groupings. Groups marked with the same capital letter do not show statistically significant differences ($P<0.05$).

We compared our attenuated *E. ictaluri* mutants with a commercial live attenuated vaccine to determine whether our mutants provide reduced virulence and improved protection against the wild type *E. ictaluri* infections. As can be seen from FIG. 2 and FIG. 3, attenuation and efficacy experiments indicated that some of our mutants performed better than AQUAVAC-ESC while others did not. Immersion immunization indicated that AQUAVAC-ESC, EiAKMut02, EiAK-Mut05, EiAKMut08, and EiAKMut13 were completely attenuated while others showed increased attenuation as compared to wild type *E. ictaluri*. Infection of immunized fish indicated that EiAKMut05 provided the best protection with no mortality in the immunized fish. Six other mutants indicated improved protection as compared to AQUAVAC-ESC. EiAKMut13 performed inferior to commercial vaccine in

TABLE 2

Summary of insertion identification results

| Mutants | Type | AN | Gene ID | Location |
|---|---|---|---|---|
| EiAKMut01 | NS | | Negative regulator of sigma E activity (rseB) | aaTA^MAR2XT7 |
| EiAKMut02 | NS | | Glycine cleavage system protein P (gcvP) | ggTA^MAR2XT7 |
| EiAKMut03 | NS | | Glycine cleavage system protein P (gcvP) | taTA^MAR2XT7 |
| EiAKMut04 | NS | | Hypothetical protein pEI1_p1 | taTA^MAR2XT7 |
| EiAKMut05 | NS | | Succinate dehydrogenase/fumarate reductase, cytochrome b subunit | tcTA^MAR2XT7 |
| EiAKMut06 | NS | | Electron transport complex protein RnfB | ggTA^MAR2XT7 |
| EiAKMut07 | NS | | Negative regulator of sigma E activity (rseB) | aaTA^MAR2XT7 |
| EiAKMut08 | NS | | Glycine cleavage system protein P (gcvP) | acTA^MAR2XT7 |
| EiAKMut09 | N | | Fimbrial chaperon protein | ggTA^MAR2XT7 |
| EiAKMut10 | N | | Putative RNA one modulator protein pEI1_p4 | atTA^MAR2XT7 |
| EiAKMut11 | N | | 2-oxoglutarate dehydrogenase E1 component | agTA^MAR2XT7 |
| EiAKMut12 | N | | Malate dehydrogenase | aaTA^MAR2XT7 |
| EiAKMut13 | S | | UDP-glucose 6-dehydrogenase | taTA^MAR2XT7 |
| EiAKMut14 | S | | TnpA | tcTA^MAR2XT7 |

NS, neutrophil and serum;
N, neutrophil;
S, serum;
AN, accession number;
^, insertion point.

terms of protection, but EiAKMut13 provided slightly greater protection against wild type infection as compared to the sham vaccinated fish.

Example

Live Attenuated Vaccine for Use in Catfish

The following description more particularly discloses the steps used in practicing the BLMS method as applied to the claimed *E. ictaluri* live attenuated vaccine.

Bacterial Strains, Plasmids, and Growth Conditions.

*Escherichia coli* SM10 λpir was used as the donor strain in conjugations for transfer of pAKgfplux2 and pMAR2XT7 into *Edwardsiella ictaluri* strain 93-146. *E. ictaluri* and *E. coli* DH5α carrying pAKgfplux2 were used as negative and positive controls in neutrophil and serum screening experiments. *E. coli* strains were grown using Luria-Bertani (LB) broth and agar plates at 37° C. and *E. ictaluri* was grown using brain heart infusion (BHI) broth and agar plates at 30° C. Antibiotics were added to the following final concentrations: ampicillin (100 μg/ml), colistin (12.5 μg/ml), gentamicin (12.5 μg/ml). 2 mM Isopropyl-β-D-thiogalactopyranosid (IPTG) was used in growth medium and screening assays to induce expression of bacterial luciferase operon (luxCD-ABE) from the lacZ promoter in pAKgfplux2. *E. ictaluri* minimal medium was used to eliminate auxotrophic mutants.

Construction of *Edwardsiella ictaluri* Mutant Library.

MAR2xT7 insertions were generated by introducing pMAR2xT7 from *E. coli* SM10 λpir into *E. ictaluri* carrying pAKgfplux2 in conjugal mating as described in Karsi, A. & Lawrence, M. L. Broad host range fluorescence and bioluminescence expression vectors for Gram-negative bacteria. *Plasmid* 57, 286-295 (2007), herein incorporated by reference. Transposants were selected on 20×20 cm LB agar plates containing 12.5 μg/ml colistin and 12.5 μg/ml gentamicin. Putative transposants were picked robotically using a Flexsys Colony Picker (GENOMIC SOLUTIONS, Ann Arbor, Mich.) into 60 μl of LB broth containing colistin and gentamicin in 384-well microtiter plates and grown overnight in HIGRO shaker (GENOMIC SOLUTIONS) at 30° C. A duplicate library was prepared by the Flexsys Colony Picker before sterile glycerol was robotically added to the cultures at a final concentration of 20%. Plates were sealed with aluminum foil to prevent cross contamination, lids were taped to prevent freeze drying, and libraries were frozen at −80° C.

Catfish Serum and Neutrophil Preparation.

Specific pathogen free (SPF) fish facility at the College of Veterinary Medicine, Mississippi State University maintains SPF channel catfish. For serum preparation, 1-2 kg SPF catfish were anesthetized in water containing 200 mg/l tricaine methane sulfonate (MS222) and blood was collected at 1% of body weight. A recovery period of one month was given for subsequent blood collections. Serum was obtained and stored at −80° C. as single use aliquots. Neutrophils were isolated from the single cell suspensions of anterior kidney cells of SPF catfish (38.63±0.68 cm, 424.20±23.34 g) using discontinuous percoll gradient centrifugation procedure described previously. Purity of neutrophils collected from the 1.060-1.080 interface was determined using flow cytometry.

In Vitro Mutant Screening Using Catfish Serum and Neutrophils.

384-well plates containing the frozen mutants were taken out from the −80° C. and aluminum cover is removed immediately. Plates were centrifuged briefly and returned to 4° C. until the culture thawed completely. Four 96-well plates containing 195 μl of BHI medium with colistin and gentamicin antibiotics and 2 mM IPTG were prepared. Five microliters of mutant bacteria were inoculated in each well and were grown at 30° C. by shaking at 250 RPM for 16-18 hours. The next day, 10 μl of mutant culture containing approximately 106 CFU was mixed with 90 μl of catfish serum containing 2 mM IPTG and plates were returned to the imaging chamber of an IVIS Imaging System 100 Series (XENOGEN CORP., Alameda, Calif.).

Initial bioluminescence of the serum was detected after five min pre-incubation of samples in the imaging chamber adjusted to 30° C. to eliminate temperature effect on light production. After initial imaging, subsequent images were captured from the same plates at every 15 min intervals during the 90 min data collection. Images were analyzed and photons emitted from each well were quantified using Living Image Software v2.50 (XENOGEN CORP.). Percent light change between the first and last measurement times was determined for each mutant and compared to serum resistant (*E. ictaluri* 93-146 pAKgfplux2) and serum sensitive (DH5α pAKgfplux2) controls included in each plate.

Neutrophil screening was accomplished by setting up phagocytosis assays including freshly isolated neutrophils with 75% or higher purity, 15% SPF catfish serum, 2 mM IPTG, and mutant bacteria. Neutrophil to bacteria numbers were adjusted to give a ratio between 1:40 and 1:80. Bioluminescence imaging was conducted as described above in the serum screening procedure. Percent bioluminescence change in 2,256 mutants was calculated and compared to those of positive and negative controls.

One hundred and eighty mutants with reduced bioluminescence were re-screened against serum and neutrophils in quadruplicate samples and data were analyzed using General Linear Model procedure of SAS v 9.1 (SAS Institute Inc., Carey N.C.). 100 mutants were selected for in-vivo screening studies.

In Vivo Mutant Screening.

SPF channel catfish (5.20±0.18 cm) were transferred from the SPF fish facility to 40 l flow-through tanks with dechlorinated municipal water. Fish were maintained in well-aerated tanks with a water temperature of 28° C. throughout the experiments. After one weak of acclimation, fish were anesthetized in water containing 100 mg/l MS222 and each mutant was injected into 15 catfish at a concentration of approximately $1 \times 10^7$ CFU in 100 μl phosphate-buffered saline (PBS). Wild-type and PBS injected fish were also included in the experiment as positive and negative controls. Fish were monitored daily and dead fish were removed from the tanks. Percent mortality rates indicated attenuation state of serum, neutrophil, and both serum and neutrophil mutants. Fourteen mutants with the highest attenuation rates were further characterized.

Determination of Virulence and Vaccine Potentials.

Virulence and efficacy of 14 mutants were characterized by infecting catfish by both intraperitoneal injection and immersion. Each 40 l flow-through tank contained twenty fish and four tanks were used for each mutant. Fish were allowed to acclimate for one week. Quadruplicate wild type and PBS controls were also included in all experiments. Bacteria numbers were adjusted to be equal by determining $OD_{600}$ readings and adjusting volumes accordingly. In the first study, fish (13.80±0.26 cm, 25.83±1.49 g) were infected by immersion in water containing $1 \times 10^6$ CFU/ml for one hour. After 21 days, immunized fish were infected with wild-type *E. ictaluri* by immersion in water with $1 \times 10^7$ CFU/ml for one hour. Fish were monitored and dead fish were removed daily. In the second study, fish (14.61±0.33 cm, 32.70±2.36 g) were anesthetized and infected by injecting $1 \times 10^5$ CFU in 100 μl PBS.

After 21 days, fish were infected by immersion as described above. Virulence and efficacy of each mutants and controls were calculated from the fish mortality rates.

Identification of Transposon Insertion Sites.

Transposon insertion sites were identified by using a single primer PCR protocol. Mutants were grown for 18 hours and genomic DNA was prepared using WIZARD Genomic DNA Purification Kit (PROMEGA). In the first round of PCR reaction, the transposon specific template was amplified linearly for 40 cycles. A second round produced specific and non-specific amplicons due to low annealing temperature at 30° C. The final round further amplified the amplicons. The 25 µl PCR reaction contained 0.2 mM dNTPs, 0.2 µM transposon specific primer, 1.5 mM MgCl2, buffer, and 1.25 units of Taq polymerase (PROMEGA). The five µl single primer PCR reaction was cleaned with 2 µl of EXOSAP-IT enzyme mix (USB CORP.) according to the manufacturer's instructions. Twenty micoliters of BIGDYE v3.1 sequencing reaction contained 2 µl of EXOSAP-IT enzyme mix treated template and 10 µM nested transposon specific primer. Transposon specific sequences were trimmed and remaining bacterial sequences were searched against nucleotide and protein databases using BLAST program.

Vaccination Studies.

Virulence and efficacy of mutants were compared to a commercial vaccine (AQUAVAC-ESC). Experiment contained 10 mutants, a mixed group containing Mut02, Mut04, Mut05, and Mut06, a commercial live attenuated vaccine, and wild-type and sham controls. Two of the mutants (Mut02 and Mut08) harbored transposon insertions in the same gene but at different locations and therefore served as an internal control in the experiments. Each 40 1 flow-through tank contained 25 fish and four tanks were assigned to each group. Fish were allowed to acclimate for two weeks before bacterial challenges. Bacteria numbers were adjusted to be equal by determining $OD_{600}$ readings and adjusting volumes accordingly. For vaccination, fish (11.62±0.16 cm, 15.36±0.65 g) were infected by immersion in water containing $2\times10^7$ CFU/ml for one hour. After 21 days, immunized fish were infected with wild-type E. ictaluri by immersion in water with $1\times10^7$ CFU/ml for one hour. Fish were monitored and dead fish were removed daily. Mean percent mortalities for each group were calculated, arcsine-transformed, and analyzed using PROC GLM procedure of SAS 9.1 (SAS Institute Inc., Carey, N.C.).

Analysis of the Mutants

Succinate-ubiquinone oxidoreductase (SQR) encoded by the sdhCDAB gene cluster and menaquinol-fumarate oxidoreductase (QFR) encoded by the frdABCD gene cluster are part of the trichloroacetic acid (TCA) cycle and are structurally and functionally related membrane-bound enzyme complexes. EiAKMut05 has an insertion in the sdhC gene, which encodes one of four subunits of the succinate dehydrogenase complex. SdhC is one of the two subunits that anchor the complex in the cytoplasmic membrane. Succinate dehydrogenase is part of the aerobic respiratory chain and the Krebs cycle, oxidizing succinate to fumarate while reducing ubiquinone to ubiquinol. It is closely related to fumarate reductase, which catalyzes the reverse reaction. Succinate dehydrogenase and fumarate reductase can replace each other at different relative rates and with different apparent substrate affinities. Because of fumarate reductase's ability to convert succinate to fumarate, sdhCDA mutant of *Salmonella enterica* serovar Typhimurium were slightly attenuated and complete attenuation was achieved by succinate dehydrogenase/fumarate reductase double mutation. In *E. ictaluri*, sdhC is the first gene in a polycistronic operon that encodes the four components of succinate dehydrogenase; therefore, it is possible that the mutation in sdhC has a polar effect on expression of downstream genes. Our results indicate that attenuation of *E. ictaluri* was achieved with sdhC mutation without a need for generating double mutants in frd genes. An explanation for this could be that fumarate reductase's ability to convert succinate to fumarate in *E. ictaluri* is not as efficient as compared to *Salmonella* and *E. coli* or *E. ictaluri* sdhC mutant is cleared from the fish before bacteria can activate fumarate reductase or anaerobic condition triggering use of fumarate reductase does not occur during fish infection. Our recent analysis of *E. ictaluri* proteome showed that many proteins involved in Tricarboxylic acid (TCA) pathway including the fumarate reductase complex present and TCA pathway significantly represented in *E. ictaluri* (unpublished data). In *E. coli* sdhC mutants, SdhC activity is located in the cytoplasm, and it utilizes artificial electron acceptors; in contrast, wild-type *E. coli* has membrane-associated SdhC activity with ubiquinone as the electron acceptor. In *E. coli*, fumarate reductase is expressed under anaerobic conditions with glucose as a carbon source. Although SdhC has similar function, hydrophobicity, and protein size to the membrane-binding subunit from fumarate reductase (FrdC), SdhC and FrdC do not share significant sequence identity. In *Helicobacter pylori*, fumarate reductase was found to be essential for colonization of mouse gastric mucosa. In *E. coli* and *Salmonella*, succinate dehydrogenase is known to contribute to pathogenicity. The organic acids formate and succinate have a protective effect in stationary phase cells against killing effects of antimicrobial peptide BPI, which appears to disrupt the bacterial respiratory chain. Maintenance of protective levels of formate and succinate requires the activity of formate dehydrogenase and succinate dehydrogenase, respectively. *E. ictaluri* also encodes the formate dehydrogenase complex in its genome.

Mutants 2, 3, and 8 all had insertions in gcvP, which encodes a protein that is part of the glycine cleavage system. The glycine cleavage system is a loosely associated four subunit enzyme complex that catalyzes the reversible oxidation of glycine to form 5,10-methylenetetrahydrofolate, which serves as a one carbon donor. It is one of two sources of 1 C units with serine hydroxymethyltransferase being the other (and is considered the more important source). Expression of the glycine cleavage enzyme system is induced by glycine, and gcv mutants are unable to use glycine as a 1 C source and excrete glycine. The glycine cleavage system is also part of the formyltetrahydrofolate biosynthesis system. GcvP is a 104 kDa protein that catalyzes the decarboxylation of glycine. In *E. ictaluri*, gcvP is the third gene in a three gene operon; it is located downstream of gcvH and gcvT, which encode subunits of the glycine cleavage system. *E. ictaluri* also has a gene that encodes serine hydroxymethyltransferase. The glycine cleavage system has not been linked with virulence previously, and our disclosed composition and method are the first to employ it.

Mutant 1 had an insertion in rseB, which encodes one of two negative regulators of sigmaE. RseA is considered the major regulator of sigmaE. SigmaE is expressed in response to heat shock and other stresses on membrane and periplasmic proteins, including misfolding of outer membrane proteins, hyperosmotic stress, metal ion exposure, changes in LPS structure, and starvation signal ppGpp. SigmaE is required for heat-induced transcription of rpoH, which encodes heat shock factor sigma32 and other heat shock proteins. RseB is a periplasmic protein that interacts with RseA. RseB stimulates binding of RseA to sigmaE, thereby assisting RseA in tethering sigmaE to the cytoplasmic membrane. Degradation of RseA releases sigmaE and allows it to interact with the core enzyme of RNA polymerase to initiate transcription. Although mutations in rseA cause increased sigmaE activity, an rseB mutant shows wild-type sigmaE activity under inducing conditions and exhibits a small increase in sigmaE activity under non-inducing conditions. In *E. ictaluri*, rseB is the third gene in a polycistronic operon. It is downstream of rpoE, which encodes sigmaE, and rseA, and it is upstream of rseC, which encodes a positive regulator of sigmaE. SigmaE is required for *Salmonella* virulence and mediates *Salmonella* resistance to oxidative stress and antimicrobial peptides. SigmaE is also required for *Salmonella* to survive intracellularly. We disclose the first report of RseB being associated with virulence.

Mutant 6 has an insertion in rsxB, which encodes one of six proteins that form a SoxR reducing system in *E. coli*. SoxR is a regulatory protein that senses superoxide and nitric oxide and induces expression of an oxidative stress response. When SoxR is activated by oxidation of its [2Fe-2S] cluster, it induces expression of SoxS, which is a transcriptional regulator that induces expression of superoxide dismutase and other oxidative response proteins. The SoxR reducing system inactivates SoxR, thereby turning off the oxidative stress response. In *E. coli*, when any of the six rsx genes are mutated, SoxS is constitutively expressed, leading to induction of oxidative stress response. In *Salmonella*, SoxS is not essential for virulence, but SoxS was found to contribute to virulence in an *E. coli* mouse pyelonephritis model. In *E. ictaluri*, rsxB is the second in the six gene rsx operon.

Mutant 4 has an insertion in a gene encoding a hypothetical protein located on one of the two *E. ictaluri* constitutive plasmids, pEI1. The protein has >50% identity with *Salmonella* effector proteins with leucine rich repeats that are secreted through a type III secretion system. The 618 amino acid protein appears to be in a monocistronic operon.

Example

Identifying Mutants that Fail to Attach to the Host Epithelium

The BLMS method can also be used to identify bacterial mutants that fail to attach to the host molecules, cells, or surfaces. Attachment and colonization of the host epithelium is an indispensable first step to any bacterial infection and can be achieved through a variety of diverse mechanisms. To investigate these attachment mechanisms in *Edwardsiella ictaluri*, we used random insertion of the pMar2xT7 transposon to generate a library of 1728 mutants. Each mutant expressed bioluminescence constitutively from the plasmid pAKlux1. This library was then screened in a high throughput fashion using an IVIS Living Image System (XENOGEN) in a series of nested in vivo challenges using a skin abrasion model we developed. Twenty mutants that displayed a decrease in their ability to colonize the channel catfish epithelium were identified. Results from this study will delineate mechanisms of *E. ictaluri* attachment to channel catfish skin and could lead to improved methods for prevention of enteric septicemia of catfish.

Combinations of Mutations.

Combinations of mutations can be constructed using the pathways we have disclosed. Specifically, in-frame deletions in TCA cycle enzymes and glycine cleavage system protein can be constructed to create greater attenuation while retaining antigenicity. Mutation of the glycine cleavage system as a vaccine strategy is a new strategy that has never been previously reported. Thus, our patenting potential is very strong for vaccine development based on glycine cleavage system. EiAKMut2 has a mutation in gcvP. The glycine cleavage system functions in providing 5,10-methylenetetrahydrofolate as a source for 1 C moieties. Our plan is to construct a mutant containing deletions in gcvP (our current mutant) and in another enzyme that serves to provide 5,10-methylenetetrahydrofolate through an alternative pathway. Knocking out both pathways should cause improved attenuation.

Mutation of genes encoding TCA cycle enzymes, exemplified by EiAKMut5 and EiAKMut12, shows great potential as a strategy for an effective live attenuated *E. ictaluri* vaccine. Knockout of genes encoding TCA cycle enzymes was recently discovered as an effective strategy for vaccine development in *Salmonella* (which is closely related to *Edwardsiella*). We have found that knocking out a single TCA cycle gene does not always cause complete attenuation, but knocking out two genes can cause complete attenuation. Specifically, a *Salmonella* sdhCDA-frdABCD mutant was fully avirulent and effective as a vaccine, while a *Salmonella* sdhCDA mutant was not fully attenuated. A combination mutant can be constructed that has deletions in sdhC (the gene mutated in EiAKMut5) and mdh (the gene mutated in EiAKMut12), as well as a second sdhC combination mutant that has a knockout in another enzyme that encodes a related TCA cycle enzyme.

Use of Other Bacterial Species as Live Attenuated Vaccines for Various Hosts

The method and compositions disclosed herein are not limited to *Edwardsiella ictaluri*, but can be used in other bacteria as well. Because the genes discovered in this research project are well conserved in bacteria, the mutation of these genes in other bacterial pathogens can be utilized for development of effective live attenuated vaccines to prevent other diseases. For example, *Salmonella enterica* is closely related to *Edwardsiella ictaluri* and is in the same bacterial family (Enterobacteriaceae). The pathogenesis of salmonellosis in mammals is also similar to the pathogenesis of enteric septicemia of catfish caused by *E. ictaluri*. The mutation of these genes in *Salmonella* will result in development of an effective live attenuated vaccine for prevention of salmonellosis in various animal hosts. Similarly, the genus *Yersinia* is also in the same family as *Edwardsiella* and *Salmonella*, and the disease pathogenesis of *Yersinia* is similar to enteric septicemia of catfish. Therefore, the mutation of these genes will be effective for development of live attenuated vaccines for *Yersinia pestis*, which causes bubonic plague in humans, *Y. enterocolitica* and *Y. pseudotuberculosis*, which cause gastrointestinal disease in humans and other mammals, and *Y. ruckeri*, which causes enteric redmouth disease in salmonid fish.

The mutation of these genes may be an effective strategy for development of live attenuated vaccines for pathogenic *Escherichia coli*, *Shigella flexneri*, and *Shigella dysenterieae*, which are also closely related to *E. ictaluri*. The mutation of these genes can also be used for development of live attenuated vaccines against *Francisella tularensis*, which causes tularemia in humans, because the disease pathogenesis is similar to enteric septicemia of catfish. Other bacterial pathogens that we anticipate mutation of these genes may be effective for development of live attenuated vaccines include *Pasteurella multocida, Mannheimia haemolytica, Histophilus somni, Haemophilus influenzae, Haemophilus ducreyi, Haemophilus parasuis, Actinobacillus pleuropneumoniae, Actinobacillus suis, Actinobacillus actinomycetemcomitans, Avibacterium paragallinarum, Moraxella catarrhalis, Moraxella bovis, Pseudomonas aeruginosa, Coxiella burnetii, Bordetella bronchiseptica, Bordetella pertussis, Bordetella parapertussis, Bordetella avium, Burkholderia mallei,*

*Burkholderia pseudomallei, Neisseria meningitidis, Neisseria gonorrhoeae, Brucella abortus, Legionella pneumophila, Helicobacter pylori,* and *Campylobacter jejuni*. Mutation of these genes may also be effective for development of live attenuated vaccines for gram-positive pathogens such as *Listeria monocytogenes*. In addition, BLMS may be an effective tool for identification of new gene targets for development of live attenuated vaccines.

Although the present invention has been described and illustrated with respect to at least one preferred embodiment and uses therefore, it is not to be so limited since modifications and changes can be made therein which are within the full intended scope of the invention.

We claim:

1. A composition for providing immunological protection from an enteric septicemia caused by *Edwardsiella ictaluri* which comprises a live attenuated strain of *Edwardsiella ictaluri*, wherein said live attenuated strain of *Edwardsiella ictaluri* is selected by introducing a gene disrupting mutation in a gene coding for a protein selected from the list consisting of glycine cleavage system (gcvP), serine hydroxymethyltransferase, succinate dehydrogenase, malate dehydrogenase, 2-oxoglutarate dehydrogenase, negative regulator of sigma E activity (rseB), hypothetical protein pEI1_p1, electron transport complex protein RnfB, Fimbrial chaperon protein, Putative RNA one modulator protein pEI1_p4, UDP-glucose 6-dehydrogenase, fumarate reductase (frdA), genes encoding enzymes in the tricarboxylic acid (TCA) cycle, and combinations thereof into an *Edwardsiella ictaluri* strain, wherein said strain of *Edwardsiella ictaluri* with said introduced gene disrupting mutation has been screened for virulence by challenging one or more live fish with said strain of *Edwardsiella ictaluri* with said introduced gene disrupting mutation, wherein a reduction in virulence as compared to a wild type *Edwardsiella ictaluri* strain identifies said strain of *Edwardsiella ictaluri* with said introduced gene disrupting mutation as said live attenuated strain of *Edwardsiella ictaluri*.

2. A live attenuated vaccine against an enteric septicemia caused by a pathogenic bacterial strain of *Edwardsiella* comprising a composition created by introducing a gene disrupting mutation in a gene coding for a protein selected from the list consisting of glycine cleavage system (gcvP), serine hydroxymethyltransferase, succinate dehydrogenase, malate dehydrogenase, 2-oxoglutarate dehydrogenase, negative regulator of sigma E activity (rseB), hypothetical protein pEI1_p1, electron transport complex protein RnfB, Fimbrial chaperon protein, Putative RNA one modulator protein pEI1_p4, UDP-glucose 6-dehydrogenase, fumarate reductase (frdA), genes encoding enzymes in the tricarboxylic acid (TCA) cycle, and combinations thereof into said pathogenic bacterial strain of *Edwardsiella*, wherein said bacterial strain of *Edwardsiella* with said introduced gene disrupting mutation has been screened for virulence by challenging one or more live fish with said bacterial strain of *Edwardsiella* with said introduced gene disrupting mutation, wherein a reduction in virulence as compared to a wild type bacteria of said bacterial strain of *Edwardsiella* identifies said bacterial strain of *Edwardsiella* with said introduced gene disrupting mutation as said live attenuated vaccine.

3. A composition for providing immunological protection to a fish from an enteric septicemia caused by *Edwardsiella ictaluri*, said composition comprises a live attenuated strain of *Edwardsiella ictaluri* comprising at least one gene disrupting mutation in a gene coding for a protein in the list consisting of glycine cleavage system (gcvP), serine hydroxymethyltransferase, succinate dehydrogenase, malate dehydrogenase, 2-oxoglutarate dehydrogenase, negative regulator of sigma E activity (rseB), hypothetical protein pEI1_p1, electron transport complex protein RnfB, Fimbrial chaperon protein, Putative RNA one modulator protein pEI1_p4, UDP-glucose 6-dehydrogenase, fumarate reductase (frdA), genes encoding enzymes in the tricarboxylic acid (TCA) cycle, and combinations thereof, wherein said strain of *Edwardsiella ictaluri* with said at least one gene disrupting mutation has been screened for virulence by challenging one or more live fish with said strain of *Edwardsiella ictaluri* with said at least one gene disrupting mutation, wherein a reduction in virulence as compared to a wild type bacteria of said strain of *Edwardsiella ictaluri* identifies said strain of *Edwardsiella ictaluri* with said at least one gene disrupting mutation as said live attenuated vaccine.

4. A composition for providing immunological protection to a fish from an enteric disease caused by a pathogenic bacterial strain of Enterobacteriaceae comprising a live attenuated strain of the pathogenic bacterial strain of Enterobacteriaceae having at least one gene disrupting mutation in a gene coding for a protein in the list consisting of glycine cleavage system (gcvP), serine hydroxymethyltransferase, succinate dehydrogenase, malate dehydrogenase, 2-oxoglutarate dehydrogenase, negative regulator of sigma E activity (rseB), hypothetical protein pEI1_p1, electron transport complex protein RnfB, Fimbrial chaperon protein, Putative RNA one modulator protein pEI1_p4, UDP-glucose 6-dehydrogenase, fumarate reductase (frdA), genes encoding enzymes in the tricarboxylic acid (TCA) cycle, and combinations thereof, wherein the pathogenic bacterial strain of Enterobacteriaceae with the at least one gene disrupting mutation has been screened for virulence by challenging one or more live fish with said pathogenic bacterial strain of Enterobacteriaceae with the at least one gene disrupting mutation, wherein a reduction in virulence as compared to a wild type bacteria of said pathogenic bacterial strain of Enterobacteriaceae identifies said pathogenic bacterial strain of Enterobacteriaceae with the at least one gene disrupting mutation as the live attenuated vaccine.

5. The composition of claim 4 wherein the pathogenic bacterial strain of Enterobacteriaceae is of the genus *Yersinia*.

6. The composition of claim 4 wherein the pathogenic bacterial strain of Enterobacteriaceae is of the genus *Salmonella*.

7. The composition of claim 4 wherein the pathogenic bacterial strain of Enterobacteriaceae is of the genus *Shigella*.

8. The composition of claim 4 wherein the pathogenic bacterial strain of Enterobacteriaceae is *Escherichia coli*.

9. The composition of claim 3 wherein the at least one gene disrupting mutation is at least two gene disrupting mutations.

10. The composition of claim 9 wherein the at least two gene disrupting mutations comprise gene disrupting mutations in the genes coding for glycine cleavage system (gcvP) and succinate dehydrogenase.

11. The composition of claim 4 wherein the at least one gene disrupting mutation is at least two gene disrupting mutations.

12. The composition of claim 11 wherein the at least two gene disrupting mutations comprise gene disrupting mutations in the genes coding for glycine cleavage system (gcvP) and succinate dehydrogenase.

13. A method of providing immunological protection to a fish from an enteric disease caused by a pathogenic bacterial strain of Enterobacteriaceae in the fish comprising providing to the fish an effective amount of a live attenuated strain of the pathogenic bacterial strain of Enterobacteriaceae having at least one gene disrupting mutation in a gene coding for a protein in the list consisting of glycine cleavage system (gcvP), serine hydroxymethyltransferase, succinate dehydrogenase, malate dehydrogenase, 2-oxoglutarate dehydrogenase, negative regulator of sigma E activity (rseB), hypothetical protein pEI1_p1, electron transport complex protein RnfB, Fimbrial chaperon protein, Putative RNA one modulator protein pEI1_p4, UDP-glucose 6-dehydrogenase, fumarate reductase (frdA), genes encoding enzymes in the tricarboxylic acid (TCA) cycle, and combinations thereof, wherein the live attenuated strain of the pathogenic bacterial strain of Enterobacteriaceae having the at least one gene disrupting mutation has been screened for virulence by challenging one or more live fish with the pathogenic bacterial strain of Enterobacteriaceae with said at least one gene disrupting mutation, wherein a reduction in virulence as compared to a wild type bacteria of said pathogenic bacterial strain of Enterobacteriaceae identifies the pathogenic bacterial strain of Enterobacteriaceae with the at least one gene disrupting mutation as the live attenuated vaccine.

14. The method of claim 13 wherein the at least one gene disrupting mutation is at least two gene disrupting mutations.

15. The method of claim 13 wherein the at least one gene disrupting mutation is an in-frame deletion.

\* \* \* \* \*